(12) United States Patent
Sarvazyan et al.

(10) Patent No.: US 7,819,824 B2
(45) Date of Patent: *Oct. 26, 2010

(54) METHOD AND A DUAL-ARRAY TRANSDUCER PROBE FOR REAL TIME MECHANICAL IMAGING OF PROSTATE

(75) Inventors: Armen P. Sarvazyan, Lambertville, NJ (US); Vladimir Egorov, Princeton, NJ (US); Suren Ayrapetyan, Lambertville, NJ (US)

(73) Assignee: Artann Laboratories Inc., Lambertville, NJ (US)

( * ) Notice: Subject to any disclaimer, the term of this patent is extended or adjusted under 35 U.S.C. 154(b) by 1486 days.

This patent is subject to a terminal disclaimer.

(21) Appl. No.: 11/146,367

(22) Filed: Jun. 6, 2005

(65) Prior Publication Data

US 2008/0221484 A1 Sep. 11, 2008

Related U.S. Application Data

(63) Continuation-in-part of application No. 11/123,999, filed on May 6, 2005.

(51) Int. Cl.
*A61B 5/103* (2006.01)
(52) U.S. Cl. .................. 600/587; 600/438; 600/559; 600/462
(58) Field of Classification Search .......... 600/438, 600/459, 462, 587
See application file for complete search history.

(56) References Cited

U.S. PATENT DOCUMENTS

| | | | |
|---|---|---|---|
| 5,036,855 A | 8/1991 | Fry | |
| 5,335,669 A | 8/1994 | Tihon | |
| 5,404,881 A | 4/1995 | Cathaud | |
| 5,423,332 A | 6/1995 | Zirps | |
| 5,524,636 A | 6/1996 | Sarvazyan | |
| 5,785,663 A | 7/1998 | Sarvazyan | |
| 5,820,559 A | 10/1998 | Ng | |
| 5,836,894 A | 11/1998 | Sarvazyan | |
| 5,922,018 A | 7/1999 | Sarvazyan | |
| 5,924,984 A * | 7/1999 | Rao | 600/373 |
| 6,004,267 A | 12/1999 | Tewari | |
| 6,117,105 A * | 9/2000 | Bresnaham et al. | 604/96.01 |
| 6,142,959 A * | 11/2000 | Sarvazyan et al. | 600/587 |
| 6,422,997 B1 | 7/2002 | Green | |
| 6,428,479 B1 | 8/2002 | Aksnes | |
| 6,561,980 B1 | 5/2003 | Gheng | |
| 6,569,108 B2 * | 5/2003 | Sarvazyan et al. | 600/587 |
| 6,695,787 B2 | 2/2004 | Hogendijk | |
| 6,718,196 B1 | 4/2004 | Mah | |

(Continued)

*Primary Examiner*—Long V Le
*Assistant Examiner*—Ellsworth Weatherby
(74) *Attorney, Agent, or Firm*—Boris Leschinsky (57) ABSTRACT

The present invention relates to a transrectal probe and method for real time mechanical imaging of a prostate. The probe is equipped with dual-array pressure sensors—one on the probe head and another on the shaft of the probe spaced away from the head with an angular and linear offset forming an S-shaped transition between the shaft and the head of the probe. The addition of the shaft pressure sensor array together with orientation tracking sensors allows precise calculation of the current head position throughout the examination of the prostate. Display means are used to guide the user in the proper manipulation of the probe in order to reduce the forces on surrounding tissues and organs and to minimize patient's discomfort.

11 Claims, 10 Drawing Sheets

U.S. PATENT DOCUMENTS 6,760,616 B2      7/2004   Hoey
6,778,690 B1      8/2004   Ladak
6,824,516 B2 *   11/2004   Batten et al. .................. 600/439
2005/0119650 A1 *   6/2005   Sanders et al. ................ 606/41
2006/0243285 A1 *  11/2006   Small ........................ 128/849

* cited by examiner

METHOD AND A DUAL-ARRAY TRANSDUCER PROBE FOR REAL TIME MECHANICAL IMAGING OF PROSTATE

CROSS-REFERENCE DATA

This application is a continuation-in-part of a co-pending U.S. patent application Ser. No. 11/123,999 filed May 6, 2005 and entitled "Method and device for real time mechanical imaging of prostate".

STATEMENT REGARDING FEDERALLY SPONSORED RESEARCH OR DEVELOPMENT

This invention was made with government support under SBIR Grant 2 R44 CA82620-02A1 awarded by the National Institutes of Health, National Cancer Institute. The government has certain rights in this invention.

BACKGROUND OF THE INVENTION

The present invention relates generally to medical devices. More specifically, it relates to a mechanical imaging system and process for examining, mapping, and diagnosing diseases of a palpable organ such as a prostate gland in a male patient, especially the prostate cancer. It is also applicable more generally to mechanical imaging of palpable tissues, including but not limited to, through natural body openings in a human being, i.e. mouth, ear(s), rectum, and other body cavities. It is also applicable to determination of a relative stiffness or elasticity of tissues. The term "patient" includes human beings and animals, both alive and dead that can be subject to mechanical imaging.

The high incidence of prostate cancer, as well as benign prostatic hyperplasia (BPH), especially among the older male population, dictates the need for effective means of early detection. Prostate cancer is the cause of death in about 30,000 men each year, making it the number two cancer killer of men in the United States, second only to lung cancer. However, if prostate cancer is detected early and treated effectively, the chance of survival of one afflicted with this disease improves significantly. Current methods of early diagnosis of prostate cancer include digital rectal examination (DRE), measurement of serum levels of prostate specific antigen (PSA), and transrectal ultrasound (TRUS) examination.

The following discussion provides useful overview of various methods described in the prior art and applicable to prostate examination and imaging. Substantial prior art is accumulated describing various devices and techniques using ultrasound for the imaging of the prostate. U.S. Pat. No. 6,561,980 by Gheng describes the methods of processing ultrasound images to cause automatic segmentation of prostate, rectum, and urethra once the transverse cross-sectional image of prostate is acquired by ultrasound means. U.S. Pat. No. 6,824,516 by Batten describes a sophisticated system for examining, mapping, diagnosing, and treating prostate diseases based on ultrasonic imaging, this patent is incorporated herein in its entirety by reference. U.S. Pat. No. 6,778,690 by Ladak describes a method of processing 2D and 3D ultrasound images to determine the prostate boundaries and is also incorporated herein by reference in its entirety as it provides useful image processing methodology.

Unfortunately, to date the experience with TRUS as a means of prostate cancer screening and staging has been disappointing. It adds little to screening by DRE and PSA, and the small improvement in prostate cancer detection does not justify its cost. As a screening test, TRUS has a low specificity and a high false positive rate. Evaluation of pathologic specimens shows that a significant fraction of tumors are isoechoic and thus indistinguishable from surrounding tissue, while many palpable tumors could not be visualized by TRUS.

The most sensitive single test for prostate cancer is measurement of serum PSA levels. However, its positive predictive value is limited. The DRE alone is even less useful. However, combining the two modalities nearly doubles the cancer detection rate. Large-scale studies of systematic screening for prostate cancer using PSA, DRE and TRUS concluded that combining PSA and DRE provided the highest sensitivity and specificity for prostate cancer diagnosis. Therefore, the combination of the two methods for prostate cancer screening is currently recommended by the AUA and American Cancer Society, and has been approved by FDA for patients between the ages of 50 and 75 years.

At the present time, digital rectal examination is the most widely used method of prostate cancer screening. Approximately 30-50% of palpable prostate nodules prove to be malignant upon pathologic evaluation. Screening trials have demonstrated that 70% of men with abnormal DRE undergoing radical prostatectomy have organ-confined cancer. A strong association between abnormal DRE and prostate cancer mortality has been demonstrated and it was suggested that screening DRE could prevent as many as 50-70% of deaths due to prostate cancer. DRE also has been shown to be the most cost efficient prostate screening method, especially when combined with PSA.

The main disadvantage of DRE is its high degree of subjectivity. The user has to instinctively relate what he or she senses by the finger to previous DRE experience. There may not be a sufficient number of skilled users available for large-scale mass prostate screenings. Another limitation of DRE is that a physician performing the examination cannot objectively record the state of the examined prostate. Therefore, it is difficult to objectively compare the results of consecutive examinations of the same prostate. The need therefore exists for a device allowing conducting the prostate examination objectively and obtaining results consistently that are independent of the skills of individual operators.

A new method of prostate imaging based on principles similar to those of manual palpation has been developed by Sarvazyan et al. and described in the U.S. Pat. Nos. 6,569,108; 6,142,959; 5,922,018; 5,836,894; 5,785,663; and 5,524,636, as well as in a co-pending U.S. application Ser. No. 11/123,999 all incorporated herein in their entirety by reference. This method, termed Mechanical Imaging, provides the ability to "capture the sense of touch" and store it permanently for later temporal correlation and trending. The essence of mechanical imaging is measurement of the stress pattern on the surface of the compressed tissue and analyzing the changes of that pattern while moving the sensor array over the examined tissue. Temporal and spatial changes in the stress pattern provide information on the mechanical structure of the examined tissue and enable 3D reconstruction of internal structures and mechanical heterogeneities in the tissue. Mechanical imaging is free of many of the disadvantages of DRE. Mechanical imaging has been shown to exceed substantially the limits of lesion size and depth detectable by conventional manual palpation techniques [Weiss R., Hartanto V, Perrotti M, Cummings K, Bykanov A, Egorov V, Sobolevsky S. "In vitro trial of the pilot prototype of the prostate mechanical imaging system", Urology, V. 58, No. 6, 2001, p. 1059-1063].

Recently, the American Urological Association issued recommendations to help physicians confirm the diagnosis of prostate cancer. According to these recommendations, a biopsy should be considered for any patient with an abnormal DRE and elevated PSA. The effectiveness and reliability of DRE are highly dependent on the skill of the user, since the finger does not provide a quantitative or objectively verifiable assessment. Thus, there is a great need for a new technology and a device to enable general practitioners and urologists alike to perform a reliable, accurate, sensitive, and quantitative assessment of the prostate using a computerized palpation-imaging device. Moreover, such accurate assessment of prostate size, shape, and elasticity is also important for diagnosing and monitoring of prostate cancer and BPH. Mechanical imaging technology and the low cost, prostate imaging device should improve significantly the ability of minimally trained individuals in primary care settings to assess, screen, and monitor prostate pathology in a reliable and valid manner in a male human, with a minimum of physical and mental discomfort.

While prior art mechanical imaging devices provided for data collection, the ability to recreate the 2D and 3D images of the prostate were limited by the insufficiently accurate information obtained from the transrectal probe with regard to the examined prostate in the course of examination. One reason for this is the sub-optimal shape of the probe device itself. Prior art probes are predominantly round and cylindrical in shape to repeat that of the rectum. Upon compressing the area about the prostate, it is difficult to obtain uniform compression of that area alone and not load surrounding tissues and organs, especially the sphincter.

The need exists for a novel method and probe adapted for uniform compression of the desired area in the vicinity of the prostate gland without compressing surrounding tissues such as a sphincter. Such compression of surrounding tissues and organs would distort data collection away from the desired area and introduce errors associated with tilting the probe and stretching the sphincter or other tissues of the rectum.

Another reason for reduced sensitivity is because the prostate can be hard to find initially and it can also shift from its original place during the examination procedure. Therefore, the prior art methods have a fundamental disadvantage in that as the examination progresses, no means are available to properly locate the prostate and then compensate for the probe position and orientation shift relative for the moving prostate.

The need exists therefore for a prostate examination means and method of use designed to eliminate the distortion in the position data of the prostate probe and make it independent of the internal movements of the prostate organ.

Finally, the need exists for devices and methods allowing training of medical personnel conducting prostate mechanical imaging.

SUMMARY OF THE INVENTION

Accordingly, it is an object of the present invention to overcome these and other drawbacks of the prior art by providing a novel method and device for objective and consistent mechanical imaging of a palpable organ eliminating the influence of operator's skills on the results of such examination.

It is another object of the present invention to provide a mechanical imaging device for examination of prostate shaped in such a way as to allow proper compression of the prostate organ only and minimizing distortions caused by pressing the device against other surrounding tissues and organs.

It is another object of the present invention to provide a mechanical imaging device for examination of prostate having dual-array pressure transducer probe, one array on the head of the probe and another on the shaft of the probe.

It is another object of the present invention to provide a probe and a method of its use allowing teaching the medical personnel the proper technique of prostate examination.

The method of the invention is based on a method of real time mechanical imaging of the prostate organ with a probe inserted through a rectum. According to one aspect of the method of the invention, generating a two- or three-dimensional prostate mechanical image from a plurality of pressure response data and probe orientation data comprises the general steps of:

locating the prostate under the transrectal probe head pressure sensor array by first identifying the sphincter with a secondary pressure sensor array located on a probe shaft, then advancing the probe until the bladder is reached and then retracting it somewhat to identify the area of probable location of the prostate, scanning the prostate by the probe head sensor array by pressing it repeatedly against the prostate, incorporating newly acquired mechanical prostate information into a two-dimensional normalized mechanical image of the prostate, including using of the sphincter as a secondary reference object, visualizing that two-dimensional normalized mechanical image of the prostate in real time to reveal possible areas of interest inside the prostate, and calculating prostate features and constructing of composite two-dimensional and three-dimensional mechanical prostate images, using an image recognition technique.

Importantly, the processing of data is preferably conducted by using data from both the probe head pressure sensor array (used as a primary or first source of pressure data) and from shaft pressure sensor array (used as a secondary source of pressure data). This allows moving of the probe relative to the prostate while maintaining the common identified features of each obtained mechanical image. In other words, every time the probe is moved from one position to the next, the processing means of the device are adapted to follow certain identifiable features and the distance from the sphincter from the previous mechanical image to the next one such that a complete 2D or 3D image may be constructed. That way, there is less need for knowing the absolute position in space of both the prostate and the probe in order to accurately relate each successive pressure pattern to a certain part of the prostate.

In the preferred embodiment, the dual-array probe and the system of the invention include: an S-shaped probe shaft with pressure sensor array for collecting pressure response data in the vicinity of the sphincter; a probe head pressure sensor array for collecting data in the vicinity of the prostate volume; a probe orientation tracking sensors for collecting a probe orientation data; a processing apparatus for processing the pressure response and orientation data to generate mechanical image data and calculate prostate features; and a display device for representation of at least a two-dimensional image of the prostate.

Importantly, the shape and size of the head pressure sensor array is selected such that it provides for uniform compression of the area of interest about the prostate gland and not other areas of the rectum. Further facilitating this aspect of the invention is the S-shaped design and an angular offset between the head of the probe and the shaft of the probe. Such advantageous shape increases the accuracy of obtained pressure data and reduces the artifacts caused by inadvertent tilting of the probe to avoid sphincter trauma.

Preferably, in order to further increase the accuracy of the results, the probe head orientation and its position relative to examined prostate is calculated from orientation data recorded from 3D magnetic sensors and a 2D accelerometer sensor, and combined with the pressure response data recorded from the head pressure sensor array and the shaft pressure sensor array.

As opposed to the devices of the prior art, the present invention takes advantage combining three independent sources of positioning information:
- using the prostate itself as a reference object by providing real time calculation and visualization of the probe head positioning relative to the examined prostate
- having more than one pressure sensor arrays working together in an integrated manner to take advantage of locating the prostate in its relationship to a nearby organ, which is more stable in its position such as sphincter, and finally
- calculating of probe head position from probe orientation data.

Combining all these sources of information, the device of the invention provides calculations including both the orientation and pressure response data. The device and method of the present invention are created with a design philosophy to create a patient-friendly system, which is easy and intuitive to use by the examining physician. As a result, the present invention advantageously provides for:
- early prostate cancer detection;
- quantitative classification of prostate geometrical and mechanical features;
- automatic identification of what has changed between successive examinations;
- tracking and trending treatment impact for certain treatment modalities;
- matching the system output with pathology findings as proof of system performance.

BRIEF DESCRIPTION OF THE DRAWINGS

A more complete appreciation of the subject matter of the present invention and the various advantages thereof can be realized by reference to the following detailed description in which reference is made to the accompanying drawings in which.

DETAILED DESCRIPTION OF THE PREFERRED EMBODIMENTS OF THE INVENTION

A detailed description of the present invention follows with reference to accompanying drawings in which like elements are indicated by like reference letters and numerals.

Figure 1:
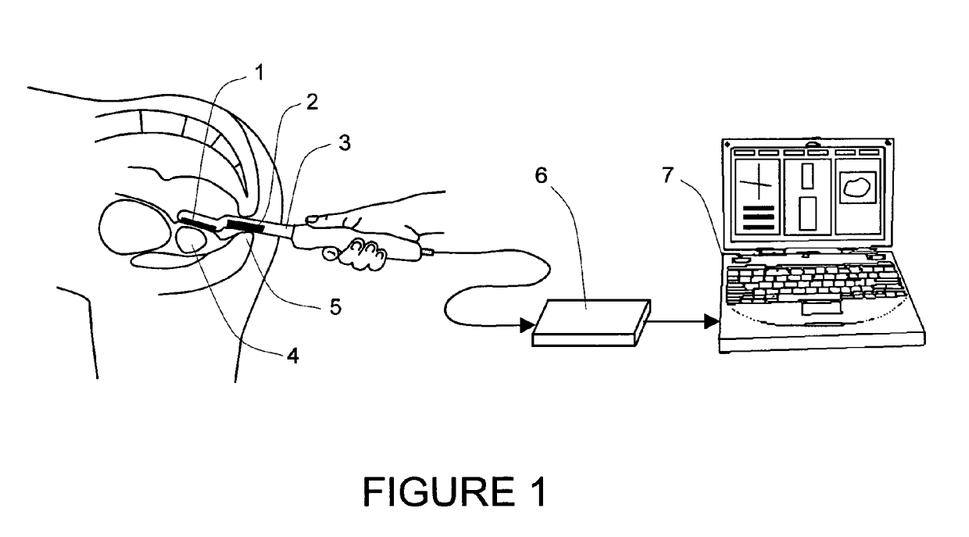
FIG. 1 is a schematic diagram illustrating the functional structure of the system in accordance with the present invention.

Referring now to the drawings, FIG. 1 is a schematic view of a preferred embodiment of a device for generating a mechanical image of a three-dimensional prostate volume from a plurality of data frames corresponding to a scan of the prostate. The device comprises the following major elements:
- a dual-array transrectal probe 3 with incorporated head pressure sensor array 1 for receiving pressure response data for the prostate 4 and shaft pressure sensor array 2 for receiving supplemental pressure response data for a sphincter area 5,
- electronic unit 6, and
- a processing and displaying means 7, which may be for example incorporated into a compact personal computer.

The prostate examination is performed using the following general steps. The patient is instructed to take off all clothes below the waist. The examination is preferably performed in the standing position by bending a patient over the examination table to form a 90-degree angle at the waist. This novel position allows the muscles in the vicinity of the examination probe to relax and has yielded better results than other examination position. In this position, patient' chest is lying on the table or another horizontal surface and patient's weight is applied to the table surface so that leg muscles are free from any tension. Optionally, the patient can also be examined while lying on his side, with his knees bent toward his chest. The probe is preferably enclosed within a disposable lubricated cover. During the insertion into the rectum, pressure applied to the anal sphincter should be monitored in order to minimize the level of patient' discomfort. Gentle posterior pressure is applied as the probe is slowly inserted with the sensor surface down. Allowing a few seconds for the external and internal sphincter to relax will avoid patient discomfort. Scanning begins in the sagitall plane by first optionally imaging the sphincter used as a supplemental reference organ. Then, the probe is inserted deeper until the bladder is visualized. Next, by sliding the probe backwards, the prostate is detected and the probe is positioned in a way that enables the device to display the prostate gland surface in the center of the screen. Once the probe is properly positioned, evaluation of prostate is performed through a set of multiple pressings on the median sulcus and lateral lobes of the prostate. In certain cases, change in an elevation angle of the probe is required to visualize the prostate.

Figure 2:
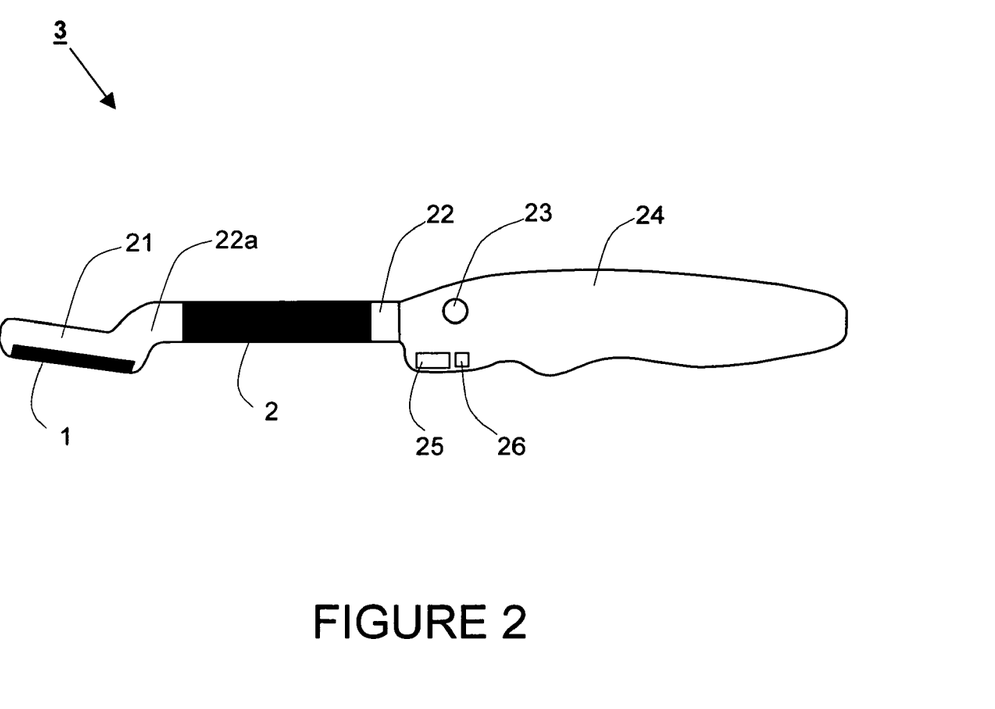
FIG. 2 is a side view of the probe with a head pressure sensor array, a shaft pressure sensor array, and orientation sensors.

FIG. 2 is a side view of the preferred embodiment of the transrectal probe 3 with the head pressure sensor array 1 installed on a probe head 21, and with the shaft pressure sensor array 2 installed on a probe shaft 22 attached to the probe handle 24. The most distal probe head section of the probe has a straight segment containing the head pressure sensor array. The length of this straight segment is preferably chosen to be about 25 mm (1 inch) to about 50 mm (2 inches)

long. This length allows proper coverage of the prostate area without interfering with the bladder or other surrounding tissues.

The shaft 22 of the probe has an S-shaped distal end 22a designed to provide a linear offset between the head of the probe and the shaft of the probe. When the probe head is compressed against the prostate, the entire probe is moved somewhat down in the direction of the prostate. The presence of this S-shaped section of the probe shaft allows not to compress tissues and organs surrounding the shaft and only to compress the prostate by pressing the probe head against thereof. Dimensions of the S-shaped distal end of the probe shaft are chosen preferably to ensure that the linear offset between the shaft and the head is ranging between about 4 mm (5/32 of an inch) and 15 mm (19/32 of an inch). In the most preferred embodiment of the invention this distance is about 10 mm.

Additional improvement in the design of the probe is in the angular offset between the longitudinal axis of the probe head and the longitudinal axis of the probe shaft. Tilting the shaft axis at about 4 to 12 degrees about the head axis further reduces the distortion of the surrounding tissues and organs when the probe head is pressed against the prostate.

Spacing apart the head pressure sensor array and the shaft pressure sensor array at a proper distance allows the probe to be used to find the estimated position of the prostate using the position of the anal sphincter. In the preferred configuration of the dual-array transrectal probe of the invention, the distance between the head pressure array and the shaft pressure array is selected to be about 40 mm (19/16 inches) to about 80 mm (3⅛ inches) as measured between the centers of the respective pressure sensor arrays. The most preferred distance is about 60 mm as this is the average distance between the sphincter and the center of a prostate.

Optional elastic disposable cover (not shown) may be used to envelop the entire surface of the probe head 21, probe shaft 22, and partly the probe handle 24. The probe handle 24 further comprises supplemental positioning means consisting of a three-axis magnetic sensor 25 and a two-axis accelerometer sensor 26. The probe also includes an examination "start-stop" button 23. Of note here is the offset of the probe head 21 relative to the probe shaft 22. It is designed such that the probe better fits with the anatomy of a human patient—only the head is pressing against the prostate and the shaft is not loading the sphincter with a down aimed force. Both the shaft and the head pressure sensor arrays are therefore better adapted to visualize the prostate and the sphincter respectively.

Figure 3A:
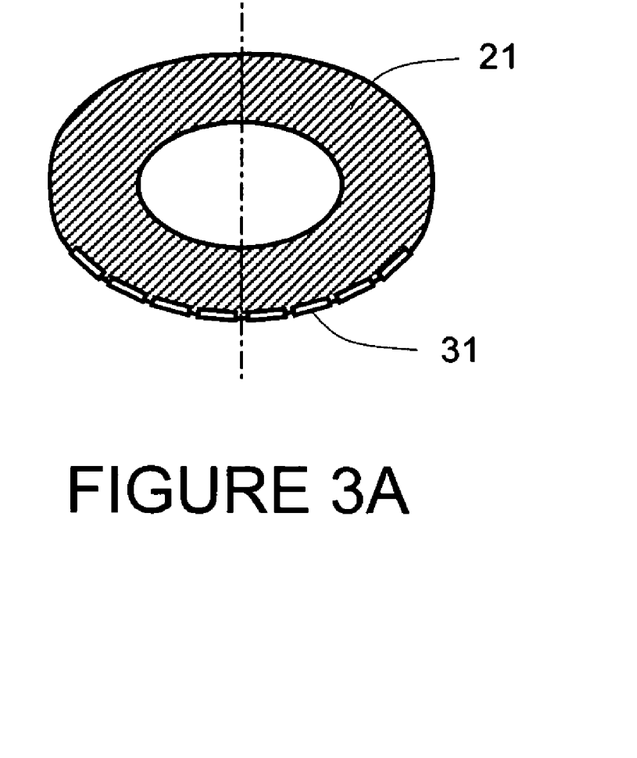
FIGS. 3A and 3B are cross-sectional views of the probe head and the probe shaft respectively in accordance with the present invention.

FIG. 3A is a preferred cross-sectional view of the preferably oblong probe head 21 with surface installed pressure sensors 31 in accordance with the present invention. As opposed to previously known devices of this type having linear pressure sensing arrays, the probe of the invention is equipped with a two-dimensional pressure sensor array. A plurality of pressure sensors 32 constitutes the pressure sensing matrix of the head pressure sensor array 1 as shown in FIG. 2. The two-dimensional pressure sensor array 1 serves the following three main purposes:

providing pressure response data in the course of examination of the prostate, providing information on changes in the probe head position relative to the prostate deploying a mechanical image recognition technique, and guiding the user during prostate examination by displaying a real time complete two-dimensional pressure pattern of the head pressure sensor array.

Size, grid, and sensor quantity in the head pressure sensor array may very. Preferably, the head pressure sensor array has a pressure sensitive area of about 12 to 20 mm wide by 30 to 50 mm long, and includes over 100 individual pressure sensors. The curvature radius of the probe head may vary too, but preferably the curvature radius should be about 10 to 20 mm to provide a uniform stress pattern while pressing against the prostate. Individual pressure sensors may be designed to be a piezoelectric, resistive, or quantum tunneling composite pressure transducer, possibly using micro-machined parts or nano-technologies. Preferably, each pressure sensor includes a capacitive pressure transducer covered by an elastic compound.

Figure 3B:
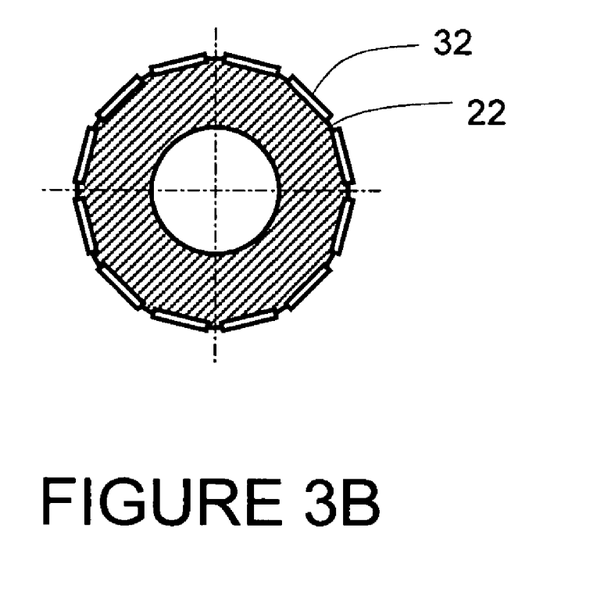

FIG. 3B is a preferred cross-sectional view of the probe shaft 22 with surface installed supplemental pressure sensors 32 in accordance with the present invention. A plurality of supplemental pressure sensors 32 constitutes the shaft pressure sensor array 2 as shown in FIG. 2. This shaft pressure sensor array serves two main purposes:

receiving supplemental pressure data from the sphincter area needed to guide the user during prostate examination by displaying a real time complete two-dimensional pressure pattern of the shaft pressure sensor array, and calculating a longitudinal position of the probe head relative to the sphincter allowing an additional correction of the probe head transversal position relative to the prostate, taking into account real time changes in probe orientation angles.

As with the head pressure sensor, the size, grid, design, and sensor quantity in the supplemental shaft pressure sensor array may very. In the most basic configuration, the shaft pressure sensor array comprises a single linear pressure array. Better functionality can be achieved by using two or preferably three linear pressure sensor arrays, especially when they are equally spaced about the outside of the shaft of the probe. In the most preferred configuration, the shaft pressure sensor array has a pressure sensitive area all the way around the probe shaft sized to be about 40 mm long and include over 100 individual pressure sensors. A shaft diameter may vary too, but preferably the shaft diameter is about 12.5 mm. Each individual pressure sensor may be a piezoelectric, resistive, or quantum tunnelling composite pressure transducer, but in the preferred embodiment it is a capacitive transducer.

Figure 4:
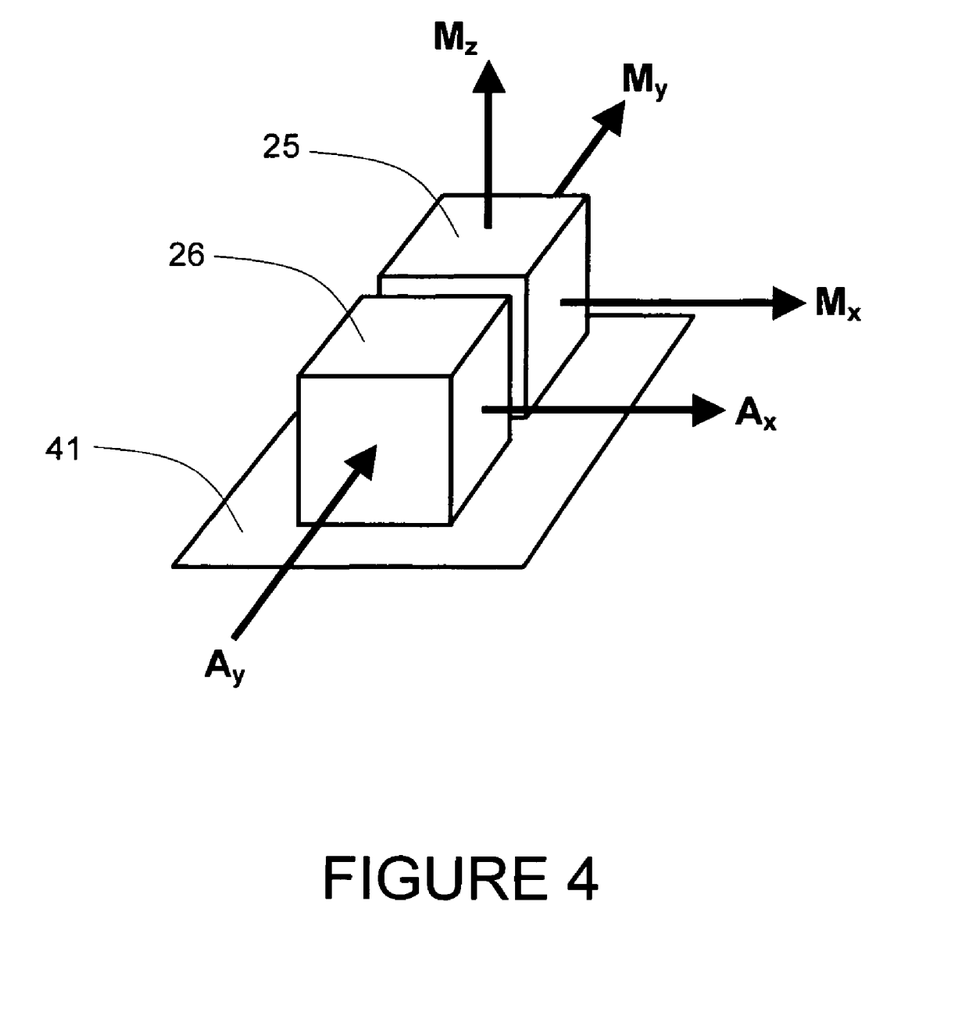
FIG. 4 is a diagram of an orientation tracking system used in the preferred embodiment of the present invention.

FIG. 4 is a diagram of an orientation tracking sensor means used in the preferred embodiment of the present invention. The orientation tracking means includes a three-axis magnetic sensor 25 with orthogonal sensitivity axes $M_x$, $M_y$, $M_z$, and a two-axis acceleration sensor 26 having sensitivity axes $A_x$, $A_y$ accordingly. Importantly, $A_x$-axis is parallel to the $M_x$-axis and $A_y$-axis is parallel to the $M_y$-axis. Both the magnetic sensor 25 and the acceleration sensor 26 are mounted on a platform 41 so that X and Y axes are parallel thereto, which in turn is parallel to the probe head pressure sensing surface. Preferably, platform 41 is incorporated inside the probe handle to be in the vicinity of the sphincter during prostate examination. Magnetic sensor readings give sensor orientation relative to Earth's magnetic field. To compensate the magnetic sensor reading for a platform tilt relative to a horizontal plane, which is perpendicular to Earth's gravity vector, it is necessary to know the platform tilt angles. The two-dimensional accelerometer sensor is used here as a tilt sensor to provide elevation ($\phi$) and rotation ($\theta$) readings. The X, Y, Z magnetic readings can be traced back to the horizontal plane by applying the rotational equations shown below:

$$Xh = X^*\cos(\phi) + Y^*\sin(\theta)^*\sin(\phi) - Z^*\cos(\theta)^*\sin(\phi) \quad (1)$$

$$Yh = Y^*\cos(\theta) + Z^*\sin(\theta) \quad (2)$$

where Xh and Yh are Earth's magnetic vector projections to the horizontal plane. Once Xh and Yh are known, it is possible to calculate an azimuth angle as:

$$\text{azimuth} = \text{arcTan}(Yh/Xh) \quad (3)$$

To facilitate the use of the accelerometer sensor as a tilt sensor, a known low-pass filter may be applied.

In use, upon pressing the "start" button on the probe handle, the processing means 7 is supplied with all angle readings and calculates current azimuth angle to set this azimuth angle as a azimuth reference angle equaling to zero. At the same time, an orientation closeness of azimuth angle discontinuity to this azimuth reference angle is calculated. In case this closeness exceeds a predetermined threshold, axes X and Y are mutually changed in equations (1), (2) to move away the azimuth angle discontinuity from a probe operation range. All azimuth angles thereafter and during prostate examination procedure are calculated relative to that azimuth reference angle so that the user may observe in real time all probe orientation angles: azimuth, elevation, and rotation.

Figure 5:
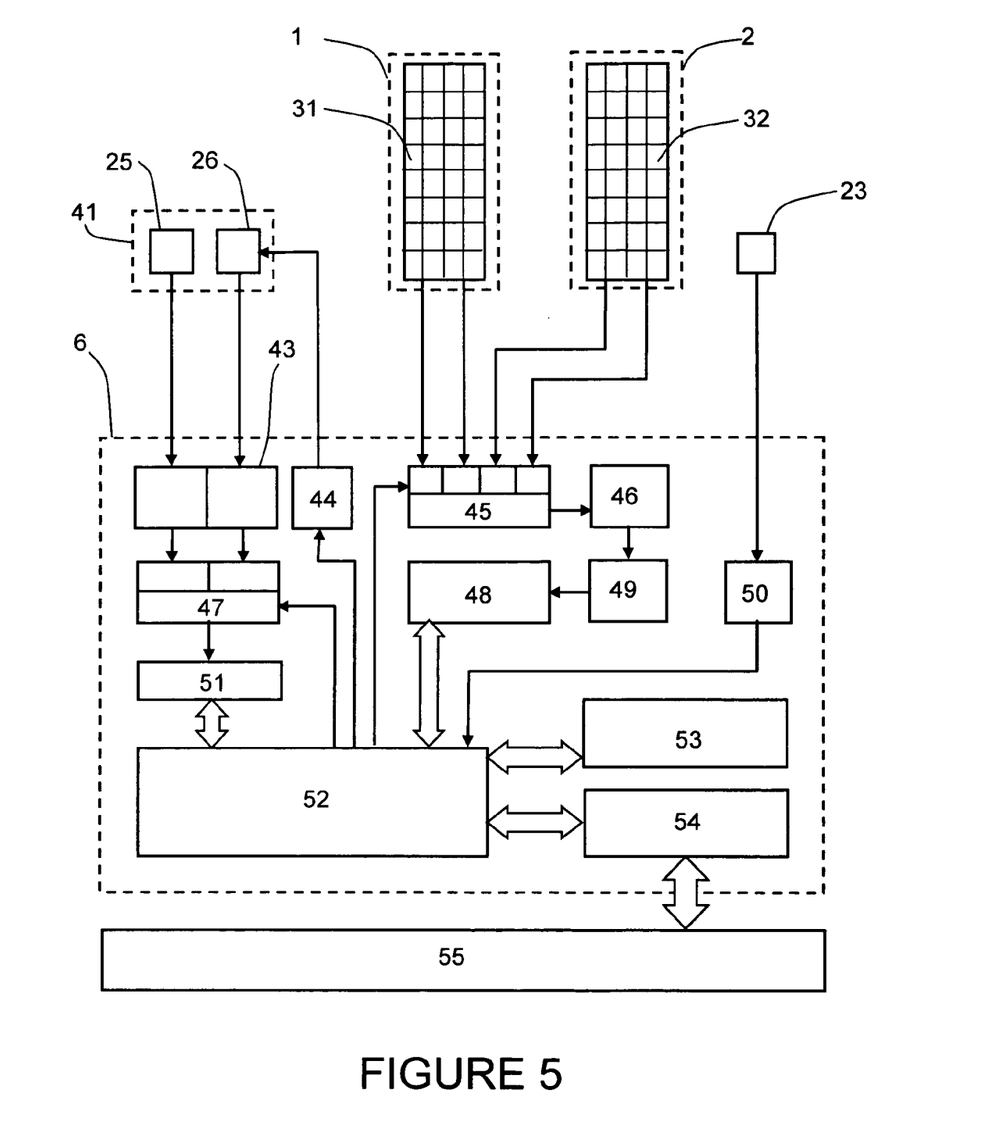
FIG. 5 represents an electronic unit schematic diagram of the device.

FIG. 5 represents a schematic diagram of an electronic unit 6 of the device in accordance with the present invention. A plurality of pressure sensors 31 forming the head pressure sensor array 1, and a plurality of pressure sensors 32 forming the shaft pressure sensor array 3 are shown on the diagram. A pressure sensing circuit inside the electronic unit 6 comprises an analog switching unit 45, amplifier 46, converter and/or integrator 49, designed to amplify and convert respective electrical signals generated by each pressure sensor for detecting a pressure imposed on each sensor during prostate examination. Analog-to-digital converter 48 transforms analog input signal into a digital signal and sends it to a processor 52. A plurality of amplifiers 43 amplify signals generated by accelerometer sensor 25 and magnetic sensor 26 described above for detecting the probe orientation during pressing against the prostate and movement of the probe from one pressing site to another. The amplified signals from amplifiers 43 are sent to multiplexer 47. Multiplexed signals are converted to digital signals by analog-to-digital converter 51 and sent to processor 52. A set/reset circuit 44 controlled by the processor 52 generates set/reset pulses supplied to magnetic sensor 26 to optimize the magnetic domains for most sensitive performance. Structure and functional characteristics of set/reset circuit 44 are determined by the type of magnetic sensor used for the design of the probe and by recommendations of specific magnetic sensor manufacturer. A control button 23 mounted on the transrectal probe handle is connected to the processor 52 through a driver 50 for controlling the prostate examination process and providing at least a stop/start function. Processor 52 communicates with analog-to-digital converters 48 and 51, multiplexers 45 and 47, and a communication port 54 to support data exchange with external processing and displaying means 55. Preferably, the external processing and displaying means 55 is a compact laptop computer. Data storage unit 53 may be used in electronic unit 6 for storing prostate examination data and intermediate information needed for proper functioning thereof, for example orientation sensor calibration data, pressure sensor calibration and tuning data, etc. The processing means is designed to automatically detect pressure sensors malfunction such as for example excessive noise and impaired sensitivity and excludes any defect sensor data from acquired pressure data frames.

The external processing and displaying means 55 is intended to serve for examination data processing. It is adapted to perform the following functions:

calculate the position of each pressure sensor during prostate examination, approximate and correct mechanical images of the prostate and surrounding tissues, separate and analyze the prostate mechanical images, determine the prostate geometrical features and mechanical features of prostate inner structures such as lesions, nodules, stiffer tissue and the like, and prepare the prostate images for visualization, as described below.

The displaying means 55 preferably has a touch screen functions to communicate with the device during prostate examination.

Figure 6:
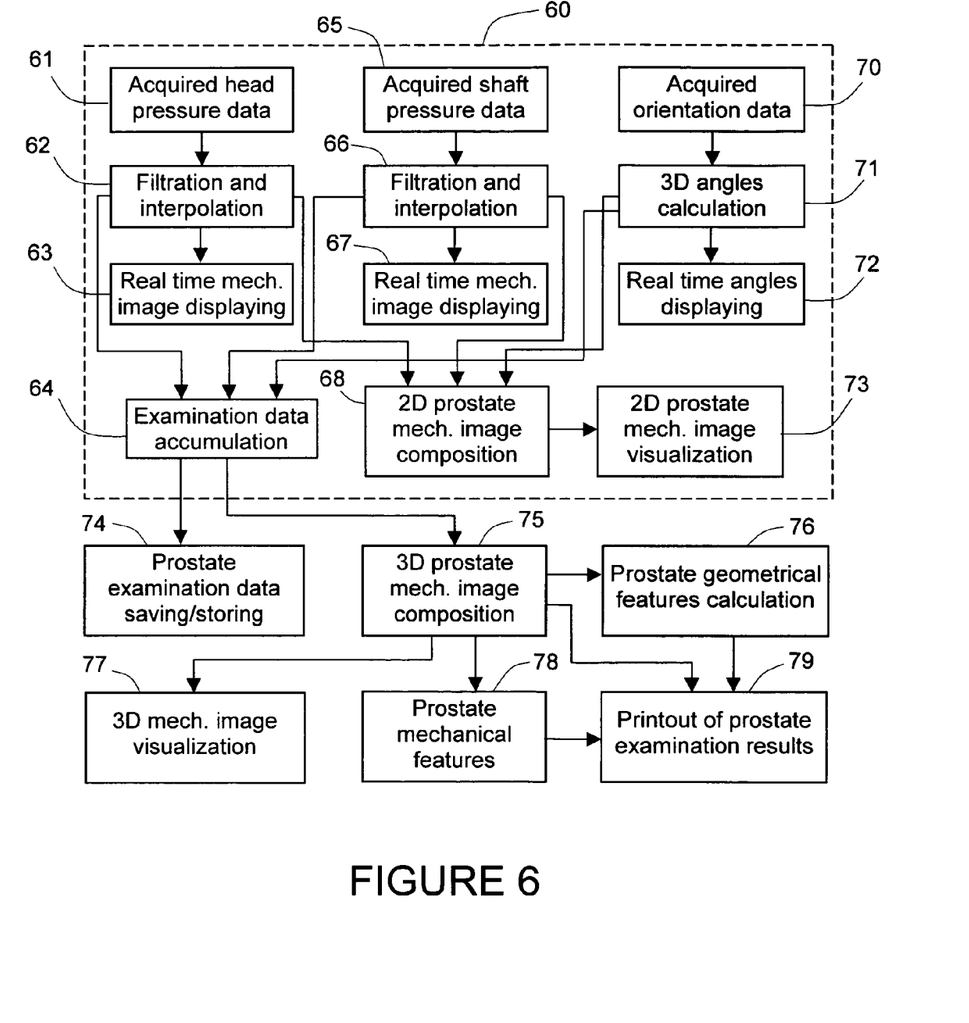
FIG. 6 is a flow chart describing steps for obtaining diagnostic information.

FIG. 6 is a flow chart describing steps for obtaining diagnostic information in accordance with the present invention. Head pressure signal is first acquired from the probe head pressure sensor array and then transformed into head pressure response data 61 expressed for example in kPa according with the sensor calibration characteristics. After temporal and two-dimensional spatial filtering in block 62, the data is displayed for the user (in block 63) in real time during prostate examination. It allows the user to guide the probe helping in detection of any abnormal or suspicious sites in the examined prostate. Shaft pressure signal is acquired from the probe shaft pressure sensor array and transformed into a shaft pressure response data 65 expressed for example in kPa according to the sensor calibration characteristics. After a temporal and two-dimensional spatial filtering in block 66, it is also displayed (block 67) in real time during prostate examination. This allows visualizing a part of sphincter area to guide the user in finding prostate and assisting in the probe navigation. Orientation data 70 is acquired from the probe orientation sensors. Further, after calculation of azimuth, elevation and rotation angles in block 71, these angles are displayed (block 72) in real time during the prostate examination to guide the user in probe navigation.

After locating the prostate under the probe head pressure sensor array, the user presses the examination start/stop button on the probe handle to start a real time prostate mechanical image composition algorithm (block 68). Description of this algorithm is given below in explanations of FIG. 9. The two-dimensional prostate mechanical image is composed and displayed in block 73. Simultaneously, the prostate examination data including that pressure response and probe orientation data are accumulated in block 64. All operations in block 60 take place in real time during prostate examination.

After completing the prostate examination, the user presses again the examination start/stop button on the probe handle to stop the real time prostate mechanical image composition algorithm, and to go to examination data saving procedure in block 74. A three-dimensional prostate mechanical image composition algorithm in block 75 is running automatically as described in detail below. The composed three-dimensional mechanical prostate image may be visualized in block 77. Prostate geometrical features and mechanical features are calculated in blocks 76 and 78 respectively. Printout of the prostate examination results (block 79) includes a series of prostate mechanical images representing the most distinctive prostate findings and quantitative prostate data such as a size, symmetry, medium groove, lesion detection classifier outputs and alike.

Figure 7:
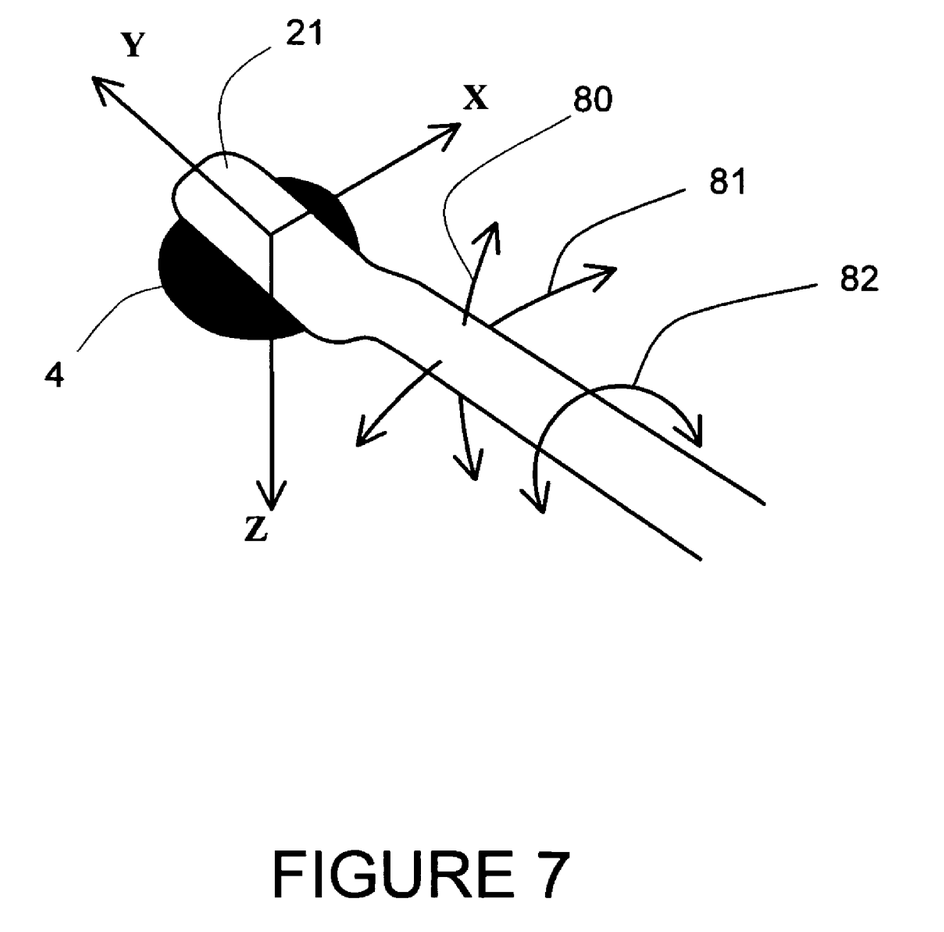
FIG. 7 is a perspective view of the transrectal probe relative to an examined prostate, illustrating a reference coordinate system having three orthogonal axes and probe orientation angles.

FIG. 7 is a perspective view of a probe relative to an examined prostate illustrating a reference coordinate system having three orthogonal axes and probe orientation angles. A processing means defines the reference coordinate system X, Y, Z at the moment of first capturing a prostate mechanical image when a total pressure prostate signal exceeds a predetermined threshold after pressing the start examination button on the probe handle. The following instant orientation angles are defined as reference angles for the reference coordinate system X, Y, Z: elevation (80), azimuth (81), and rotation (82). All subsequent probe orientation angles relative to the reference system X, Y, Z are calculated relative to these reference angles. The probe head 21 is pressed against the prostate 4, when the first capturing a prostate mechanical image occurs. In a preferred method of the invention, a probe rotation angle should be maintained close to zero. Despite of the presence of the probe head pressure sensing surface curvature, the mechanical image projection along X-coordinate on X,Y-plane is done without taking into account that curvature. The probe head mechanical image is acquired as a 2D image and used for prostate image reconstruction inside a defined three-dimensional prostate volume. For the simplicity of real time calculations, the two axes X and Y of the reference coordinate system X, Y, Z are positioned in the mechanical image plane of the probe head pressure sensor array, while the third reference or Z-coordinate is perpendicular to the mechanical image plane.

Figure 8:
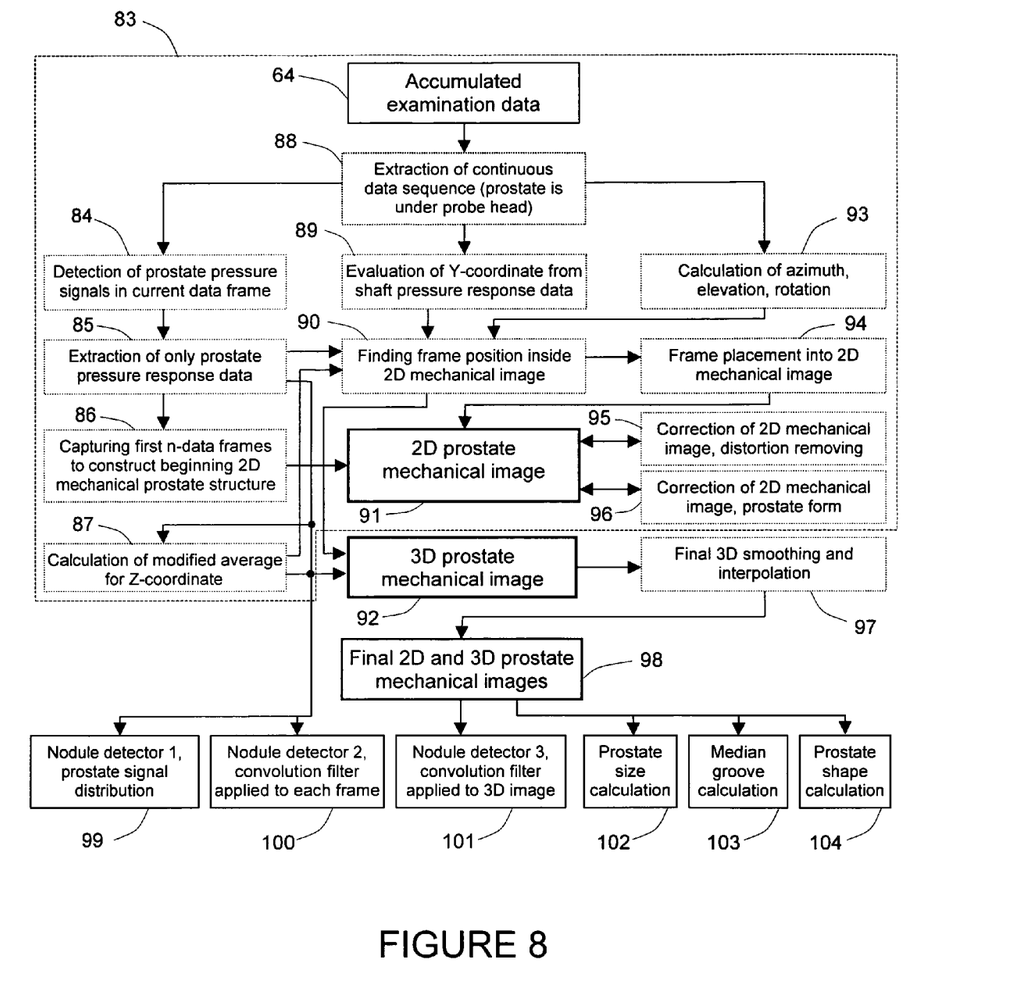
FIG. 8 is a flow chart describing steps for composition of two-dimensional and three-dimensional prostate mechanical images and calculating prostate features.

FIG. 8 is a flow chart describing the steps necessary for composition of a two-dimensional and a three-dimensional prostate mechanical image and calculating prostate features. These algorithms can be activated in real time during prostate examination as marked by dashed line 83 or after the examination is complete when all examination records are available (block 64). The first step is includes extraction of continuous pressure data sequence from the head pressure sensor array by means for calculating an individual two-dimensional pressure data frame when the prostate is located under the probe head, so that this data will only be used in prostate image composition. The extraction may be done automatically or manually by looking at examination process dynamics. Another purpose of this extraction is to exclude sphincter signals from the head pressure data during the probe insertion into the rectum.

The next step is done by the means for calculating of individual pressure imprints of the prostate on the transrectal probe of the invention. Such means initiate detection of prostate pressure imprint in each analyzed pressure data frame recorded from the head pressure sensor array (block 84). These means include an algorithm, which estimates the probability that mechanical image has a pressure signal increase in its central part. The possibility that some sensors could produce an erroneous signal, as well as that some rows and column in the sensor array could have incorrect tuning or calibrating are taken into account. Such column and row errors may cause false pressure jumps or gaps in the pressure data. For each interior row or column of the sensor array, the detection algorithm calculates a pressure signal value relative to the linear interpolation based on the boundary pressure. A predetermined number of points with highest and lowest pressure values are discarded. The positive or negative sign of the sum of remaining values defines the sign of the entire line. Each line (row or column) is assigned a certain weight, the highest for the central lines, and the lowest for boundary lines. If the sum of the weights for all lines with corresponding signs is greater than a predefined value, it is considered that the mechanical image contains the prostate imprint. The sum is then normalized to a predetermined range, using two scale parameters, which gives a quantitative estimation of the presence of a prostate imprint in the mechanical image. If no prostate pressure signal was detected inside the analyzed pressure data frame, this data frame is discarded. On the opposite, if the prostate pressure signal was detected, the next procedure in block 85 activates extraction of only the prostate pressure response data (pixels) inside analyzed pressure response data frame.

The procedure for isolation of a prostate image consists of separation of one or several relatively big coherent zones containing a relatively high pressure signal. Another purpose of this procedure is to reduce the influence of boundary effects and suppression of pressure peaks in the top and bottom parts of the sensor array corresponding to the sphincter and bladder pressure signals. This procedure starts with quadrupling the number of pixels in the image using two by two interpolations between neighboring sensors. The binary image of the pressure pattern is created by setting all pixels for which the pressure is higher than average to black. At the same time, the pixels for which the pressure is lower than average are set to white. Two types of filtering are applied thereafter to the binary image. The expanding filtering calculates the number of black pixels adjacent to each white point. If the number is higher than the predetermined value, it turns the white point into a black point in order to enlarge the black regions and cover small white holes. The squeezing filtering is applied next to achieve the same but opposite effect for black points. It calculates the number of white pixels adjacent to each black point. If that number is higher than the predetermined value, it turns it to the white point in order to squeeze black zones and smooth their edges. A sequence of expanding and squeezing removes or significantly reduces small boundary defects, eliminates the inner white holes, combines and rounds large inside zones. The resulting black zone is mapped back to the pressure sensor array, and only the pressure sensors, which belong to the black zone, are allowed to participate in the next phase of prostate image analysis.

Important advantage of the present invention is its ability to use the prostate itself as a reference object. After determination of prostate imprints earlier in the sequence, this is accomplished in the next few steps by the means for constructing of the composite prostate image. Specifically, in the procedure 86 the first n-frames of pressure response data are captured to construct a first pass two-dimensional mechanical prostate structure. This capture is occurring when the total pressure prostate signal exceeds a predetermined threshold. After averaging, the captured first pass prostate structure is transferred into a two-dimensional composite prostate image 91. After that, each subsequent pressure response data frame carrying the prostate pressure response data is analyzed in blocks 90 and 94 for placing new pressure response information into the two-dimensional composite prostate image. Block 90 runs a matching algorithm trying to find best fit of a current prostate pressure response image inside the two-dimensional composite prostate image. Preferably, the best fit is calculated by maximizing a functional F $$F(n,m) = \sum_{i,j=0}^{i=k,j=l} S_{i,j} * P_{n+i,m+j} \quad (4)$$

for $$n \subset (-k/4 + k/4), m \subset (-l/4, +l/4)$$

where k and l are quantities of horizontal and vertical pixels inside the pressure frame with the current prostate mechanical image, n and m are maximum possible image shift in pixels relative to a previous fitted mechanical image, $S_{i,j}$ is current pressure response signal of i,j pixels, and $P_{n+i,m+j}$ is a pressure signal of n+i,m+j pixel inside the two-dimensional composite prostate image.

After the best fit is found, each pixel of a current mechanical prostate image is placed into the two-dimensional composite prostate image with a predetermined weighted factor if its current value exceeds respective pixel value inside the two-dimensional composite prostate image (block 94). Preferably, all calculations in blocks 86, 90, 91, and 94 are implemented with normalized pixels, so that each pixel value of the prostate mechanical image is divided by a modified average of analyzed pressure data frame calculated inside block 87. The modified average $\overline{S}$ is calculated according to equation (5) after removing a predetermined quantity (b) of pressure pixels $S^{max}$ having maximum values.

$$\overline{S} = \left( \sum_{i,j=0}^{i=k,j=l} S_{i,j} - \sum_{q=0}^{q=b} S_q^{max} \right) / (k*l - b) \qquad (5)$$

where k and l are quantities of horizontal and vertical pixels inside the pressure response frame with the analyzed prostate mechanical image, $S_{i,j}$ is an instant pressure signal of i,j pixels.

Azimuth, elevation, and rotation angles calculated for the instant pressure response data frame in block 93, and evaluated Y-coordinate from shaft pressure data in block 89 are used in finding a frame local reference position inside the two-dimensional mechanical image space to start matching algorithm in the accordance with equation (4). Simultaneously, a procedure 95 of removing image distortion and procedure 96 of correction of the two-dimensional mechanical image 91 are run during prostate examination. The procedure 95 smoothes any distortions above a predetermined threshold in the calculated a two-dimensional gradient field inside the image 91. Procedure 96 corrects a prostate form if prostate form distortion exceeds the bounds of an acceptable prostate form variety.

Each pressure data frame carrying a prostate image is included into a three-dimensional mechanical prostate image 92 in accordance with positioning in X,Y-plane as calculated in block 90 and Z-coordinate, which is considered proportional to the calculated in block 87 modified average for current frame 87. More detailed description of the three-dimensional image composition algorithm of this block is given below in the description for FIG. 10.

After prostate examination is complete, a procedure 97 of a final smoothing and three-dimensional interpolation is applied to current image 92. The final two-dimensional and three-dimensional mechanical prostate images are then prepared in block 98 representing a plurality of contour, slices, iso-surfaces and alike for a better visual perception. Such prostate features as prostate size (small/medium/large) 102, medium groove (absent/present) 103, prostate shape (symmetrical/asymmetrical) 104 are calculated directly from the final prostate image by testing these value to a predetermined acceptance criteria.

A nodule classifier includes three nodule detectors. First of them, shown in block 99, analyzes a signal distribution for prostate pressure data to detect specific features typical for a positive nodule presence. Second nodule detector, shown in block 100, applies a series of predetermined convolution filters to each two-dimensional prostate mechanical image to detect a nodule from a variety of possible nodule forms. Preferably, a form of a convolution filter corresponds to what is being looked for in a nodule form. A third nodule detector, shown in block 101, applied a series of three-dimensional convolution filters to the final three-dimensional prostate image in block 98. Presence of specific three-dimensional objects inside a filtered prostate image signals a possible nodule presence and its location.

Figure 9:
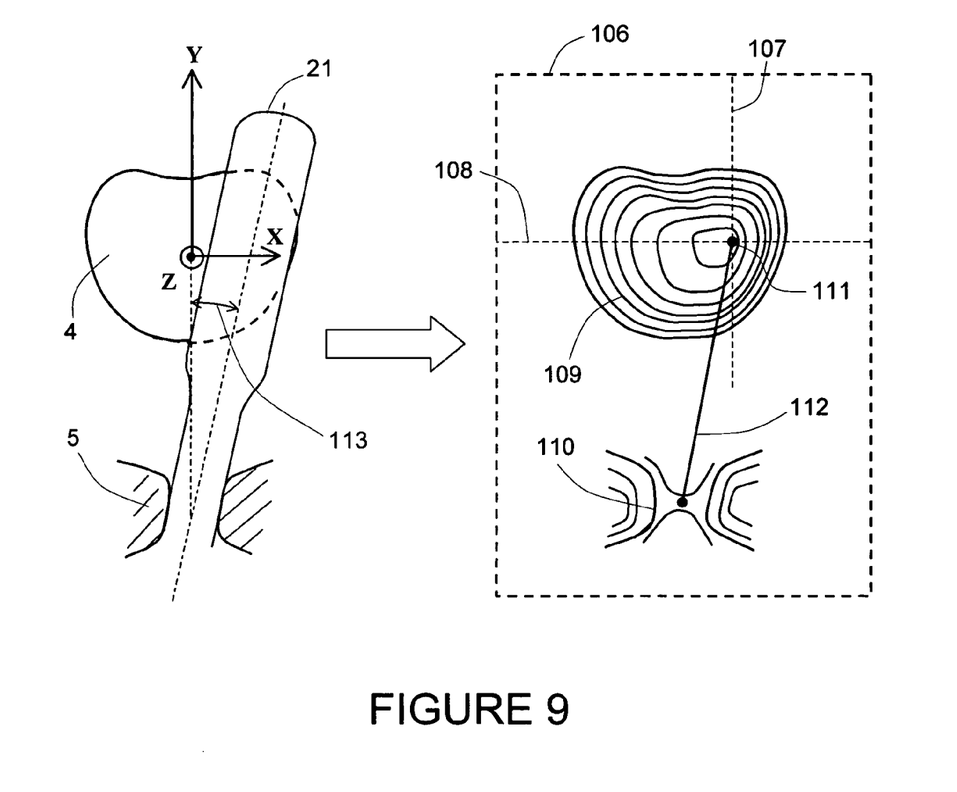
FIG. 9 is an illustration of real time two-dimensional prostate image and sphincter area mechanical image with relative probe positioning to guide the use of the probe during prostate examination.

FIG. 9 is an illustration of a sample real time two-dimensional prostate and sphincter area mechanical image with a relative probe positioning to guide the user during prostate examination. Multiple pressings of probe head 21 against the prostate 4 allow the head pressure sensor array to obtain pressure response data for the prostate. This pressure response data is then transformed into a composite two-dimensional mechanical prostate image 109 as described in FIG. 8 (block 91). At the same time, the shaft pressure sensor array provides supplemental mechanical data for the sphincter area, which is visualized in the same image frame 106 as a two-dimensional sphincter mechanical image 110. Using procedures in blocks 89, 90, and 93 described in FIG. 8, current coordinates 107, 108 of a probe head center 111 in the reference coordinate system X, Y, Z, as well as probe azimuth angle 113, and distance 112 between a sphincter center and the probe center 111 are then calculated. Combined visualization of the prostate image 109, the sphincter image 110 and the probe head position facilitates the prostate probe navigation and provides efficient feedback to the user.

Since orientation tracking system of the present invention provides only orientation angles including azimuth angle 113, it is important to use the shaft pressure sensor array to detect the position of the sphincter center and use it as a reference point to calculate the movements of the probe head. Initial position of the probe is assigned the azimuth angle value of zero as corresponding to the first pressing of the probe head against the prostate. Knowing the distance between the sphincter center as detected by the shaft sensor array and the current azimuth angle 113, the new coordinate of the probe head can be calculated from that distance by multiplying it by sinus of the azimuth angle value.

Figure 10:
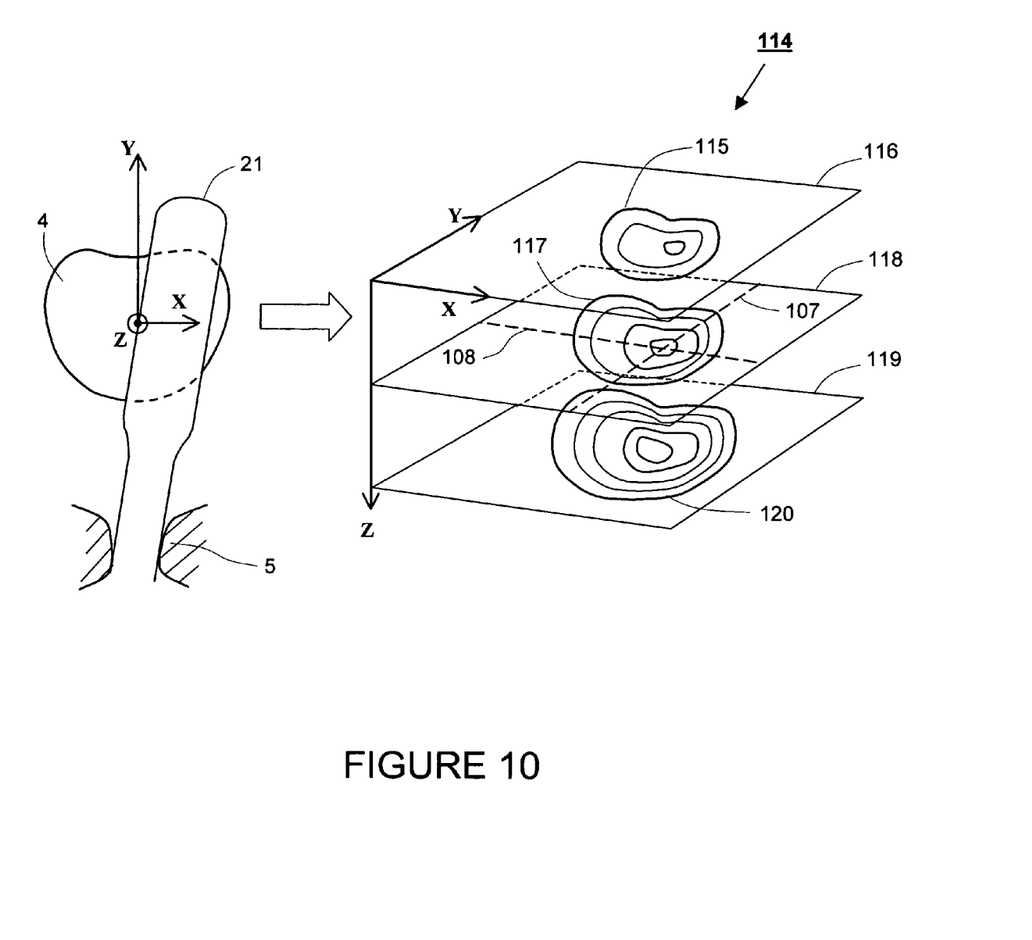
FIG. 10 is an illustration of a three-dimensional prostate mechanical image composition.

FIG. 10 is an illustration of a three-dimensional prostate mechanical image composition in accordance with the method of the present invention. The three-dimensional prostate mechanical image 114 (see also the description of block 92 in FIG. 8 above), includes a plurality of two-dimensional mechanical prostate images 115, 117, 120 placed inside planes 116, 118, 119 accordingly. During prostate scanning by multiple pressings of probe head 21 against the prostate 4, the head pressure sensor array provides pressure response data for the prostate. Each new pressure response data frame is transformed into a two-dimensional mechanical prostate image in the accordance with procedure 85 and X, Y-frame coordinates for example 107, 108 as calculated by procedure 90 and Z-coordinate as calculated by procedure 87 from FIG. 8. Each pixel of this pressure response data frame is then placed inside a two-dimensional mechanical prostate image for example 117 with a predetermined weighted factor if its current pixel value exceeds a threshold value inside the two-dimensional prostate image 117. Preferably, two different three-dimensional mechanical prostate images are constructed: one image includes only normalized pressure response pixels (each pixel value of the prostate mechanical image is divided by a modified average of analyzed pressure response data frame), while another image includes only absolute pressure response pixels.

The presence of the shaft sensor array can also be used for teaching purposes using either patient models or practicing live prostate evaluations. Low contact forces between the probe and the tissues about the patient's rectum is the goal of such training in order to minimize patient's discomfort. Shaft pressure sensor array may be successfully used to measure the level of various forces implied by the probe on the sphincter and other tissues and organs (with the exception of the prostate itself). These forces can be displayed in real time for the user so that adjustments to the position of the probe can be made to minimize such forces during the examination.

Although the invention herein has been described with respect to particular embodiments, it is understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

What is claimed is as follows:

1. A dual-array transrectal probe system for mechanical imaging of a prostate comprising:

a probe head sized to fit inside a rectum and equipped with a two-dimensional head pressure sensor array adapted to obtain a head pressure response data when said probe head is pressed against said prostate, the head pressure sensor array including a plurality of individual head pressure sensors, a probe shaft attached to said probe head to form a transrectal probe, said probe shaft including a shaft pressure sensor array adapted to obtain a shaft pressure response data, the shaft pressure sensor array including a plurality of individual shaft pressure sensors that provide a pressure sensitive area all the way around the probe shaft, an electronic unit connected to said transrectal probe and adapted to receiving said head and shaft pressure response data, and a processing and display means connected to said electronic unit, said processing and display means
configured to generate a mechanical image of said prostate from at least said head pressure response data,
data and calculate the position of a sphincter from said shaft pressure response data, and
and further configured for simultaneous displaying in real time of said mechanical image of the prostate and said position of the sphincter spaced apart from said prostate during the examination thereof.

2. The system as in claim 1, wherein said probe head further includes orientation tracking means adapted to provide positional and angular data of the location of said probe head.

3. The system as in claim 2, wherein said processing and display means is further configured for tracking the position and direction of movement of said probe head from said orientation tracking means in combination with said shaft pressure response data.

4. The system as in claim 1, wherein said processing and display means is further configured for generating at least a two-dimensional mechanical image of said sphincter.

5. A method for examining a patient's prostate, the method comprising the following steps:

(a) providing a dual-array transrectal probe that includes (i) a probe head equipped with a two-dimensional head pressure sensor array and (ii) a probe shaft equipped with a shaft pressure sensor array;

(b) displaying in real time (i) a head mechanical image generated from head pressure response data provided by the head pressure sensor array and (ii) a shaft mechanical image generated from shaft pressure response data provided by the shaft pressure sensor array;

(c) inserting the dual-array transrectal probe the into the patient's rectum;

(d) locating the patient's sphincter under the shaft pressure sensor array of the dual-array transrectal probe by reference to the displayed shaft mechanical image;

(e) locating the patient's prostate under the head pressure sensor array of the dual-array transrectal probe according to a known spatial relationship between the patient's prostate and the patient's sphincter; and (f) pressing the head pressure sensor array of the dual-array transrectal probe against the patient's prostate to create a mechanical image of the patient's prostate.

6. The method as in claim 5, wherein locating the patient's prostate under the head pressure sensor array of the dual-array transrectal probe further comprises (i) advancing the dual-array transrectal probe in the patient's anal canal until the dual-array transrectal probe reaches the patient's bladder and (ii) retracting the dual-array transrectal probe to locate the patient's prostate under the head pressure sensor array of the dual-array transrectal probe.

7. The method as in claim 5, wherein pressing the head pressure sensor array of the dual-array transrectal probe against the patient's prostate comprises adjusting the position of the dual-array transrectal probe to minimize forces exerted on the patient's sphincter and other tissues and organs.

8. The method as in claim 5, wherein the head pressure sensor array and the shaft pressure sensor array each have centers, and the center of the head pressure sensor array is located a distance of about 40 mm to about 80 mm from the center of the shaft pressure sensor array.

9. The method as in claim 8, wherein the center of the head pressure sensor array is located a distance of about 60 mm from the center of the shaft pressure sensor array.

10. The method as in claim 8, wherein:

the probe head of the dual-array transrectal probe has a distal end and a proximal end and defines a longitudinal probe head axis, and the probe shaft of the dual-array transrectal probe defines a longitudinal probe shaft axis and has an S-shaped distal end attached to the proximal end of the probe head, the S-shaped distal end defining a linear offset between the longitudinal probe head axis and the longitudinal probe shaft axis.

11. The method as in claim 10, wherein the S-shaped distal end of the probe shaft is shaped to define an angular offset between the longitudinal probe head axis and the longitudinal probe shaft axis.

* * * * *